United States Patent
Hawkins et al.

(10) Patent No.: US 8,465,525 B2
(45) Date of Patent: Jun. 18, 2013

(54) POSTERIOR PROCESS DYNAMIC SPACER

(75) Inventors: John Riley Hawkins, Raynham, MA (US); Amie Borgstrom, San Francisco, CA (US); William L. Dunbar, Bethlehem, CT (US); Seungkyu Daniel Kwak, Raynham, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 112 days.

(21) Appl. No.: 12/817,552

(22) Filed: Jun. 17, 2010

(65) Prior Publication Data

US 2011/0015676 A1   Jan. 20, 2011

Related U.S. Application Data

(62) Division of application No. 10/796,359, filed on Mar. 9, 2006, now Pat. No. 7,763,073.

(51) Int. Cl.
*A61B 17/70* (2006.01)

(52) U.S. Cl.
USPC .......................................................... 606/248

(58) Field of Classification Search
USPC .................... 623/17.11–17.16; 606/247–249
See application file for complete search history.

(56) References Cited

U.S. PATENT DOCUMENTS

| | | | |
|---|---|---|---|
| 1,985,032 A | 12/1934 | Hoult | |
| 2,677,369 A | 5/1954 | Knowles | |
| 3,648,691 A | 3/1972 | Lumb | |
| 3,805,443 A | 4/1974 | Duncan, Jr. | |
| 4,759,670 A | 7/1988 | Linder | |
| 5,011,484 A | 4/1991 | Breard | |
| 5,180,393 A | 1/1993 | Commarmond | |
| 5,403,316 A | 4/1995 | Ashman | |
| 5,496,318 A | 3/1996 | Howland | |
| 5,609,634 A | 3/1997 | Voydeville | |
| 5,616,142 A | 4/1997 | Yuan | |
| 5,645,599 A * | 7/1997 | Samani | 623/17.16 |
| 5,725,582 A | 3/1998 | Bevan | |
| 5,836,948 A * | 11/1998 | Zucherman et al. | 606/249 |
| 5,860,977 A | 1/1999 | Zucherman | |
| 5,876,404 A | 3/1999 | Zucherman | |
| 5,993,484 A * | 11/1999 | Shmulewitz | 623/1.11 |
| 6,048,342 A | 4/2000 | Zucherman | |
| 6,068,630 A | 5/2000 | Zucherman | |
| 6,074,390 A | 6/2000 | Zucherman | |
| 6,090,112 A | 7/2000 | Zucherman | |
| 6,149,652 A | 11/2000 | Zucherman | |

(Continued)

FOREIGN PATENT DOCUMENTS

| | | |
|---|---|---|
| DE | 3113142 | 1/1982 |
| EP | 322334 | 2/1992 |

(Continued)

OTHER PUBLICATIONS

Hoshi, "Expansive Cervical Laminoplasties—Observations on Comparative Changes in Spinous Process Lengths Following Longitudinal Laminal Divisions Using Autogenous Bone or Hydroxyapatite Spacers", Spinal Cord, 1996, pp. 725-728, vol. 34, Issue 12.—Abstract only.

(Continued)

*Primary Examiner* — Anu Ramana

(57) ABSTRACT

An interspinous spacer having a memory metal extension.

8 Claims, 9 Drawing Sheets

U.S. PATENT DOCUMENTS

| | | | |
|---|---|---|---|
| 6,152,926 A | 11/2000 | Zucherman | |
| 6,156,038 A | 12/2000 | Zucherman | |
| 6,183,471 B1 | 2/2001 | Zucherman | |
| 6,190,387 B1 | 2/2001 | Zucherman | |
| 6,193,757 B1 * | 2/2001 | Foley et al. | 623/17.16 |
| 6,235,030 B1 | 5/2001 | Zucherman | |
| 6,238,397 B1 | 5/2001 | Zucherman | |
| 6,280,444 B1 | 8/2001 | Zucherman | |
| 6,332,882 B1 | 12/2001 | Zucherman | |
| 6,364,883 B1 | 4/2002 | Santilli | |
| 6,379,355 B1 | 4/2002 | Zucherman | |
| 6,402,750 B1 | 6/2002 | Atkinson | |
| 6,406,478 B1 | 6/2002 | Kuo | |
| 6,419,676 B1 | 7/2002 | Zucherman | |
| 6,419,677 B2 | 7/2002 | Zucherman | |
| 6,440,169 B1 | 8/2002 | Elberg | |
| 6,451,019 B1 | 9/2002 | Zucherman | |
| 6,451,020 B1 | 9/2002 | Zucherman | |
| 6,478,796 B2 | 11/2002 | Zucherman | |
| 6,500,178 B2 | 12/2002 | Zucherman | |
| 6,514,256 B2 | 2/2003 | Zucherman | |
| 6,530,926 B1 | 3/2003 | Davison | |
| 6,582,433 B2 | 6/2003 | Yun | |
| 6,626,944 B1 | 9/2003 | Taylor | |
| 6,652,534 B2 | 11/2003 | Zucherman | |
| 6,660,038 B2 | 12/2003 | Boyer, II | |
| 6,669,697 B1 | 12/2003 | Pisharodi | |
| 6,695,842 B2 | 2/2004 | Zucherman | |
| 6,699,246 B2 | 3/2004 | Zucherman | |
| 6,699,247 B2 | 3/2004 | Zucherman | |
| 6,712,819 B2 | 3/2004 | Zucherman | |
| 6,733,534 B2 | 5/2004 | Sherman | |
| 6,761,720 B1 | 7/2004 | Senegas | |
| 6,796,983 B1 | 9/2004 | Zucherman | |
| 7,011,685 B2 * | 3/2006 | Arnin et al. | 623/17.16 |
| 7,029,473 B2 | 4/2006 | Zucherman | |
| 7,048,736 B2 | 5/2006 | Robinson | |
| 7,101,375 B2 | 9/2006 | Zucherman | |
| 7,186,254 B2 | 3/2007 | Dinh | |
| 7,189,234 B2 | 3/2007 | Zucherman | |
| 7,442,208 B2 | 10/2008 | Mathieu | |
| 7,530,991 B2 | 5/2009 | Nekozuka | |
| 2001/0031965 A1 | 10/2001 | Zucherman | |
| 2002/0029039 A1 | 3/2002 | Zucherman | |
| 2002/0143331 A1 | 10/2002 | Zucherman | |
| 2004/0153071 A1 | 8/2004 | Zucherman | |
| 2004/0167520 A1 | 8/2004 | Zucherman | |
| 2005/0143738 A1 | 6/2005 | Zucherman | |

FOREIGN PATENT DOCUMENTS

| | | |
|---|---|---|
| EP | 1330987 | 3/2005 |
| WO | WO 9004948 | 5/1990 |
| WO | WO 9942051 | 8/1999 |
| WO | WO 03015645 | 2/2003 |
| WO | WO 03071966 | 9/2003 |

OTHER PUBLICATIONS

Nakano, "Spinous Process-Splitting Laminoplasty Using Hydroxyapatite Spinous Process Spacer", Spine, Mar. 1992; pp. S41-S43, vol. 17 (3 Suppl).

Yang, "Biomechanical Comparison of the Stable Efficacy of Two Anterior Plating Systems", Clinical Biomechanics, 2003, pp. S59-S66, vol. 18.

Kubo, "Biomechanical Evaluation of Cervical Double-Door Laminoplasty Using Hydroxyapatite Spacer", Spine, 2003, pp. 227-234, vol. 28, No. 3.

Wallice Brochure, product believed to be introduced in 1986.

Grant Skidmore, X-Stop Interspinous Process Distraction (IPD), St. Francis Medical Technologies, Inc., product believed to have received FDA approval in 2005.

Vitallium Surgical Appliances, Misc. Orthopedic Appliances, 1959, p. 5, Section VI.

Khoueir, "Classification of Posterior Dynamic Stabilization Devices", Neurosurg. Focus, 2007, vol. 22(1), E3, pp. 1-8.

* cited by examiner

POSTERIOR PROCESS DYNAMIC SPACER

CONTINUING DATA

This divisional application claims priority from co-pending U.S. Ser. No. 10/796,359, filed Mar. 9, 2006, entitled Posterior Process Dynamic Spacer, (Hawkins), the specification of which is incorporated by reference in its entirety.

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint.

In some cases, when a patient having a collapsed disc moves in extension (e.g., leans backward), the posterior portion of the annulus fibrosus may further compress and extend into the spinal canal. This condition (called "spinal stenosis") produces a narrowing of the spinal canal and impingement of tissue upon the spinal cord, thereby producing pain.

There have been numerous attempts to provide relief for these afflictions by providing a spacer that inserts between adjacent spinous processes present in the posterior portion of the spinal column. In general, these interspinous implants are adapted to allow flexion, rotation, translation and lateral bending movement in the patient, but resist or limit extension.

U.S. Pat. No. 6,068,630 ("Zuchermann") discloses a spinal distraction implant that alleviates pain associated with spinal stenosis by expanding the volume in the spinal canal or neural foramen. Zucherman discloses a plurality of implants having a body portion and lateral wings. The body portion is adapted to seat between the adjacent spinous processes, while the wings are adapted to prevent lateral movement of the body portion, thereby holding it in place between the adjacent spinous processes. The designs disclosed in FIGS. 15, 80 and 84 of Zuchermann comprise central body having an integral wing.

Although the Zucherman device achieves spinal distraction, it nonetheless possesses some limitations. First, it is a multi-piece design, and so is subject to wear and implantation complexity. Second, since the Zuchermann central bodies have at least one integral wing, the clinician may encounter difficulty in sizing the central body independently of delivering the lateral wings. Third, the expansive geometry of the disclosed devices may not lend itself to minimally invasive surgical techniques seeking to conserve muscle mass and soft tissue in the regions adjacent the spinous processes.

SUMMARY OF THE INVENTION

The present inventors have developed a number of flexible interspinous devices having improvements over the conventional devices.

In a first embodiment, the extensions on one side of the implant are made of a shape memory metal. This implant is inserted into the interspinous space in a collapsed, low temperature form. When the implant rises to the temperature of the patient's body, the upper and lower extensions made of memory metal transform to the austenitic phase to extend upwards and downwards respectfully, thereby bracketing the upper and lower spinous processes and locking the implant in place.

In addition, since the shape memory extensions can deform elastically in their austenitic phase, the ends of the extensions on a lateral side of the implant can be forced together, inserted through the interspinous space, and then released, thereby allowing the extensions to spring back to their unconstrained shape.

Therefore, in accordance with the present invention, there is provided an interspinous implant for insertion into an interspinous space between adjacent spinous processes, comprising:
 a) a central body having an upper surface for bearing against an upper spinous process, a lower surface for bearing against a lower spinous process, and first and second side portions,
 b) a first upper extension extending upward from the first side portions,
 c) a second upper extension extending upward from the second side portion, the upper extensions collectively defining an upper bracket, and
 d) a first lower extension extending downward from the first side portion,
 e) a second lower extension extending downward from the second side portion, the lower extensions collectively defining a lower bracket,
 wherein each of the first upper and first lower extension comprises a shape memory metal.

In a second embodiment, the implant has bases fastened to opposite sides of the same spinous process, and the bases are connected by a flexible cord. The cord is adapted to have a flexibility and resiliency such that, during extension (when the spinous processes move closer towards one another, the flexible cord provides a soft stop for the movement of the opposite spinous process, thereby gently limiting excessive extension.

Therefore, in accordance with the present invention, there is provided an interspinous implant for insertion into an interspinous space between a first and second spinous process, the first spinous process having a first and second side, the implant comprising:
 a) a first base having a side surface adapted for fixation to a first side of the first spinous process,
 b) a second base having a side surface adapted for fixation to a second side of the first spinous process,
a first flexible ligament having a first end connected to the first base and a second end connected to the second base.

In a third embodiment, the implant is a three-piece device having a central body and a pair of lateral extensions, wherein the extensions are slid through axial slots in the central body. Because neither extension is integrally formed to the central body, the physician can first view and assess the placement of the central body prior to adding the extensions without being shielded by the extension.

Therefore, in accordance with the present invention, there is provided an interspinous implant for insertion into an interspinous space between a first and second spinous process, the implant comprising:
 a) a central body having:
  i. an upper surface for bearing against an upper spinous process,
  ii. a lower surface for bearing against a lower spinous process,
  iii. first and second side surfaces, and
  iv. first and second axial through-holes, each through-hole extending from the upper surface to the lower surface,
 b) a first extension having an upper end and a lower end, the first extension extending through the first axial through-hole of the central body, c) a second extension having an upper end and a lower end, the second extension extending through the second axial through-hole of the central body, wherein the upper ends of the extensions collectively define an upper bracket, and wherein the lower ends of the extensions collectively define a lower bracket.

In a fourth embodiment, the implant is a three-piece device having a central body and a pair of lateral extensions, wherein side surfaces of the central body are connected to the extensions. As with the third embodiment, because neither extension is integrally formed to the central body, the physician can first view and assess the placement of the central body prior to adding the extensions without being shielded by the extension.

Therefore, in accordance with the present invention, there is provided an interspinous implant for insertion into an interspinous space between a first and second spinous process, the implant comprising:

a) a central body having:
 i. an upper surface for bearing against an upper spinous process,
 ii. a lower surface for bearing against a lower spinous process,
 iii. first and second side surfaces defining a transverse axis, and
 iv. a first opening extending from the first side surface into the body,
b) a first extension having an upper end, a lower end, an inner surface, the first extension being separate from the central body,
c) a second extension having an upper end, a lower end, an inner surface, the second extension being separate from the central body, wherein the first side surface of the central body contacts the inner surface of the first extension, wherein the second side surface of the central body contacts the inner surface of the second extension, wherein the upper ends of the extensions collectively define an upper bracket, and wherein the lower ends of the extensions collectively define a lower bracket.

In a fifth embodiment, the interspinous implant has a pair of U-shaped hooks adapted to cradle the opposing processes and a connection piece therebetween. The hooks have leading and trailing ends and are further adapted to be slid laterally around the spinous process.

Therefore, in accordance with the present invention, there is provided an interspinous implant for insertion into an interspinous space between a first and second spinous process, the implant comprising:

a) an upper hook having a leading end, a trailing end, an upper bearing surface adapted to bear against the first spinous process, and a lower surface,
b) a lower hook having a leading end, a trailing end, and a lower bearing surface adapted to bear against the first spinous process, and an upper surface,
c) a central body having:
 i. an upper surface adapted for connection to the lower surface of the upper hook, and
 ii. a lower surface adapted for connection to the upper surface of the lower hook.

DETAILED DESCRIPTION OF THE INVENTION

Figure 7:
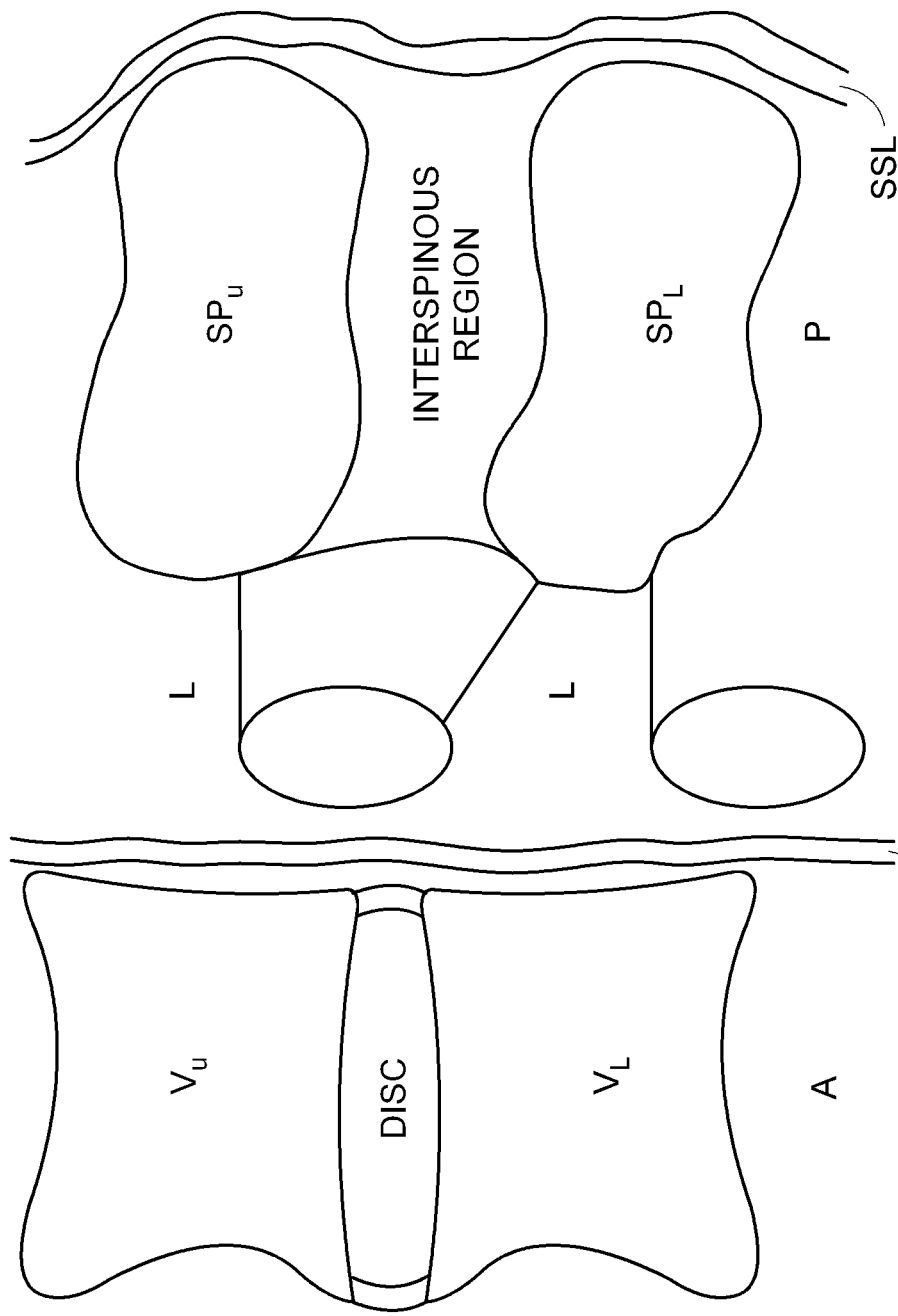
FIG. 7 is a side view of a functional spinal unit of the human anatomy.

For the purposes of the present invention, the term "interspinous" refers to the volume located between two adjacent spinous processes of adjacent vertebrae. The terms "anterior" and "posterior" are used as they are normally used in spinal anatomy. Accordingly, the "anterior" portion of the interspinous device is that portion rests relatively close to the spinal cord, while the "posterior" portion of the interspinous device is that portion rests relatively close to the skin on the patient's back. Now referring to FIG. 7, there is provided an anatomic "functional spinal unit" or FSU comprising an upper vertebrae having an upper vertebral body $V_U$ and an upper spinous process SPu, a lower vertebra having a lower vertebral body $V_L$ having a lower spinous process $SP_L$. The vertebral bodies lies in the anterior A portion of the FSU, while the spinous processes lie in the posterior portion P of the FSU. Disposed between the vertebral bodies is a disc space DISC. Disposed between the spinous process is an "interspinous region". Disposed between the spinous process and the vertebral body of each vertebra is a lamina L. The supraspinous ligament SSL lies posterior to the spinous processes. The posterior longitudinal ligament PLL lies posterior to the vertebral bodies.

Figure 1A:
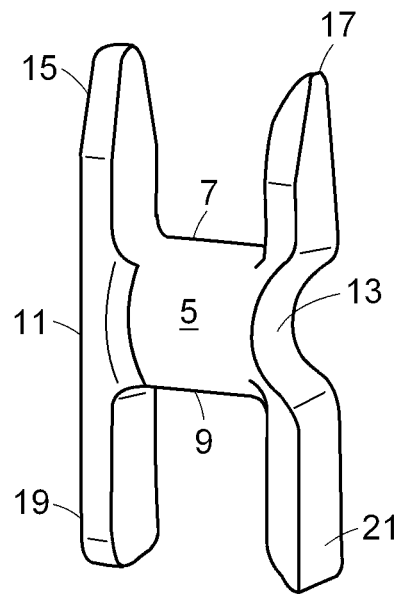
FIGS. 1a and 1b disclose embodiments of the same memory metal implant of the present invention in the austenitic and martensitic phases.

Now referring to FIG. 1a, there is provided an interspinous implant 1 for insertion into an interspinous space between adjacent spinous processes, comprising:

a) a central body 5 having an upper surface 7 for bearing against an upper spinous process, a lower surface 9 for bearing against a lower spinous process, and first 11 and second 13 side portions,
b) a first upper extension 15 extending upward from the first side portion,
c) a second upper extension 17 extending upward from the second side portion, the upper extensions collectively defining an upper bracket, and
d) a first lower extension 19 extending downward from the first side portion,
e) a second lower extension 21 extending downward from the second side portion, the lower extensions collectively defining a lower bracket, wherein each of the second upper and second lower extensions comprises a shape memory metal.

Figure 1B:
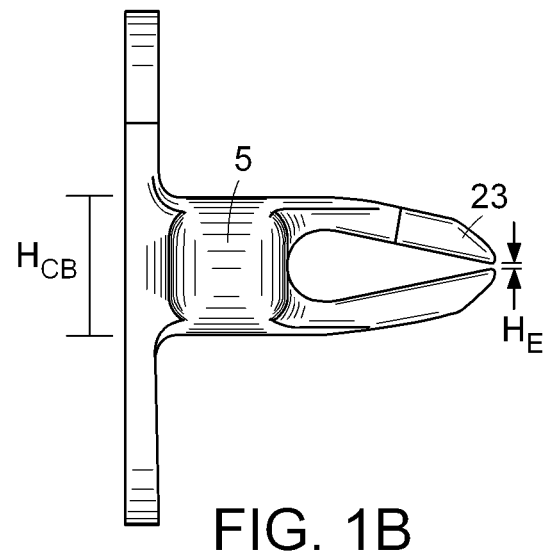

In some preferred embodiments, the first upper and first lower extensions are adapted to extend upwards and downwards in an austenitic phase, and laterally in the martensitic phase. This implant is inserted into the interspinous space in a collapsed, low temperature (martensitic) form, as shown in FIG. 1b. Now referring to FIG. 1a, when the implant rises to the temperature of the patient's body, the upper and lower extensions made of memory metal transform to the austenitic phase to extend upwards and downwards respectfully, thereby bracketing the upper and lower spinous processes and locking the implant in place.

Figure 2:
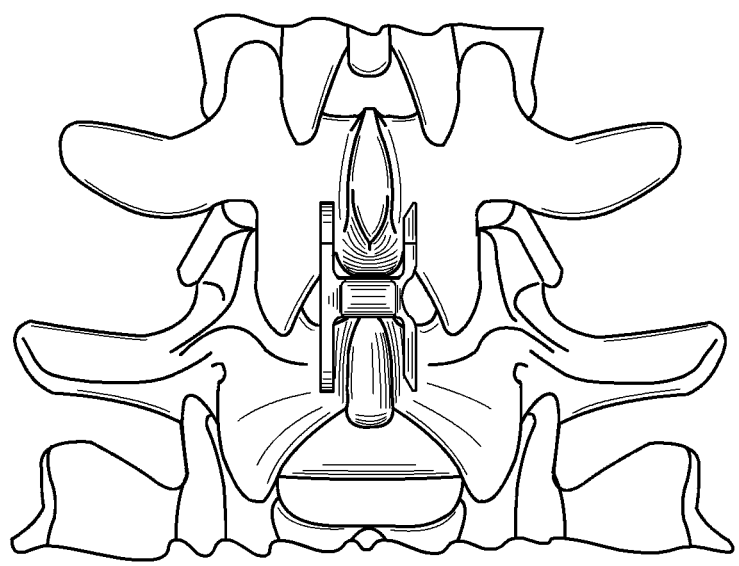
FIG. 2 discloses the memory metal implant of FIG. 1 after being implanted in the interspinous space and returning to its austenitic form.

The austenitic and martensitic forms of the implant are respectively shown in FIGS. 1a and 1b. The device as implanted is shown in FIG. 2.

Because the memory-metal induced transformation of each of the second upper and second lower extensions occur in response to a change in temperature, the desired shape changes occur without any action from the surgeon. Accordingly, the implantation of this device is very simple.

In one preferred embodiment, the side surface of the central body from which the memory metal extensions extend has a slight recess. This recess reduces the stress produced by the transformation.

In some embodiments, the implant is a unitary body. The unitary nature of the body provides for ease of manufacturing and implantation, and reduces the stress on the implant.

In some embodiments, the first upper and first lower extensions are adapted to superelastically extend sideways in a martensitic phase. This embodiment provides for a reduced stress upon the implant.

In some embodiments, at least one of the memory metal extensions has a chamfered end 23. The chamfer increases the ease of insertion on these extensions into the interspinous space. In preferred embodiments, each of the first upper and first lower extensions has a chamfered end.

In some embodiments, the upper and lower surfaces of the central body define a body height $H_{CB}$, wherein each of the first upper and first lower extensions have an end defining an extension height therebetween $H_E$, and wherein the extension height $H_E$ is less than the central body height $H_{CB}$. When the extension height $H_E$ is less than the central body height $H_{CB}$, the implant may more easily be implanted into the interspinous space. Preferably, each end of the second upper and second lower extensions contact one another in the martensitic phase.

Preferably, the shape memory material is a nickel-titanium alloy.

Figure 3A:
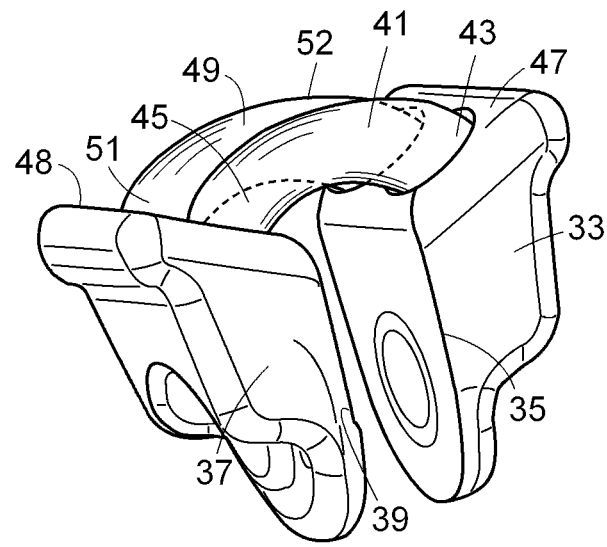
FIGS. 3a and 3b disclose a second embodiment of the present invention having two flexible cords between two bases.
Figure 3B:
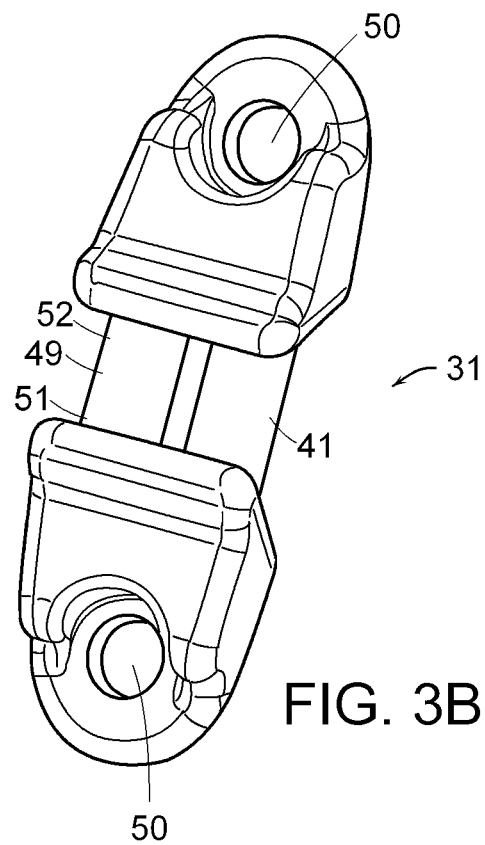

Now referring to FIGS. 3a and 3b, there is provided an interspinous implant 31 for insertion into an interspinous space between a first and second spinous process, the first spinous process having a first and second side, the implant comprising:
 a) a first base 33 having a side surface 35 adapted for fixation to a first side of the first spinous process,
 b) a second base 37 having a side surface 39 adapted for fixation to a second side of the first spinous process, and
 c) a first flexible ligament 41 having a first end 43 connected to the first base and a second end 45 connected to the second base.

Figure 3C:
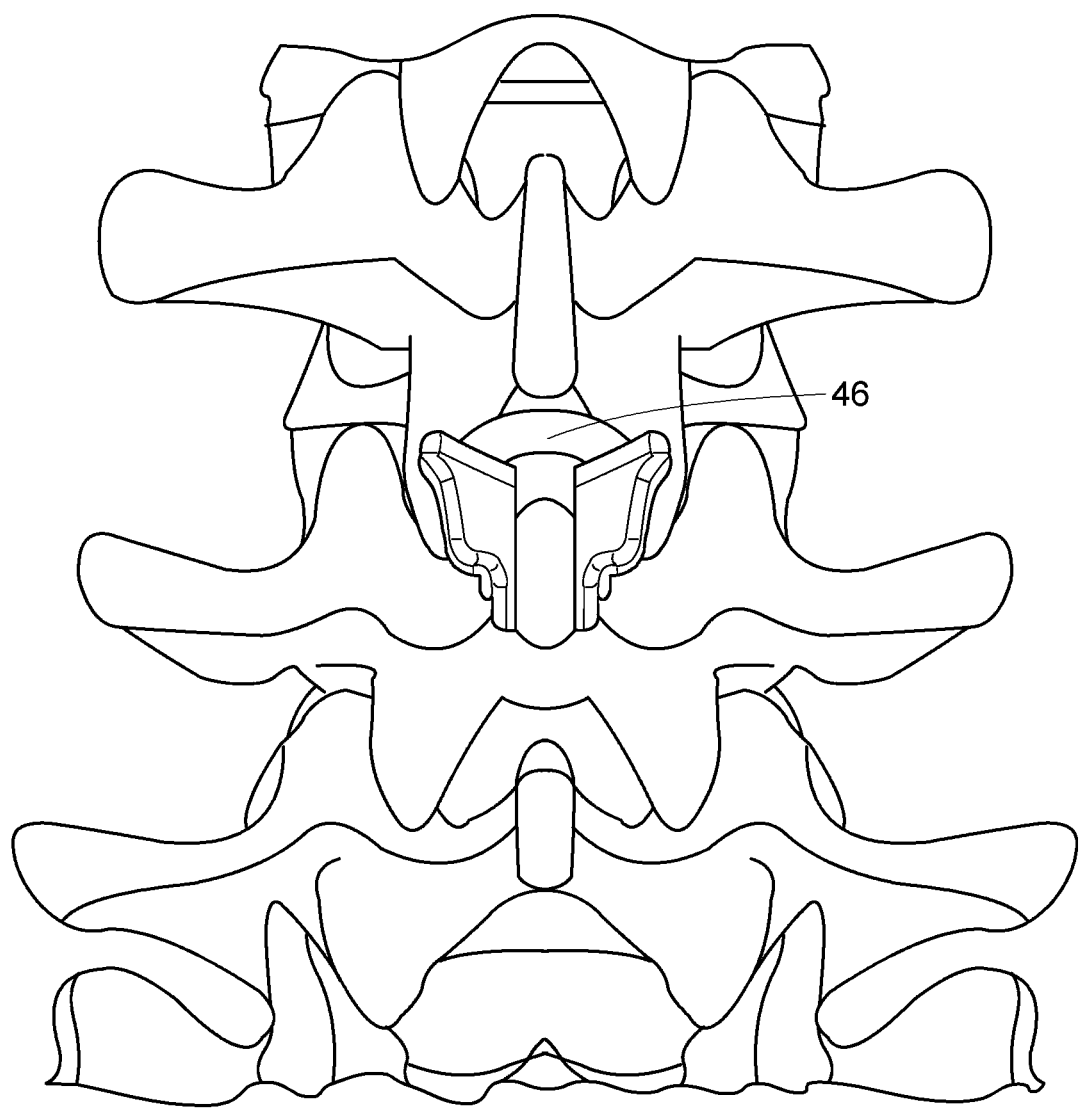
FIG. 3c discloses the implant of FIGS. 3a-b implanted so as to laterally span an interspinous space to provide a soft stop for a spinous process during extension.

Now referring to FIG. 3a, in this embodiment, the implant has bases adapted to fasten to opposite sides of the same spinous process, and the bases are connected by a flexible cord. The surgeon simply takes the implant in its open form (as in FIG. 3b), inserts the leading base of the implant laterally into a first side of the interspinous space, and then pulls the leading end as it emerges from the second side of the interspinous space. The surgeon then folds the implant so that each base abuts its respective side of the lower spinous process. Now referring to FIG. 3c, the surgeon then adjusts the position of the device so that its apex 46 of the ligament is at a position between the spinous processes that will provide the appropriate amount of distraction for the patient's relief of pain. The surgeon then fastens the bases to the lower spinous process.

The cord has flexibility and resiliency such that, during extension (when the spinous processes move closer towards one another, the flexible cord provides a soft stop for the movement of the opposite spinous process, thereby gently limiting excessive extension. Since the limitation on extension is provided gradually and gently (i.e., it is not a hard stop), it is believed that there will be less wear of the respective contacting surfaces, thereby prolonging the life of the implant.

Referring to FIG. 3a, in some embodiments, each of the first and second bases comprises an upper surface 47,48, wherein the first end of the first flexible ligament is connected to the upper surface of the first base, and the second end of the first flexible ligament is connected to the upper surface of the second base. When the ligament is connected to the upper surfaces of bases (as opposed to the side surfaces), the length of and stresses upon the ligaments are minimized.

In some embodiments, the upper surfaces of each base form an angle of no more than 180 degrees, preferably less than 180 degrees, more preferably between 100 degrees and less than 180 degrees. In this range, the ligament takes on an arcuate shape well suited to flexibly accept and resist extension of the upper spinous process.

In some embodiments, the implant further comprises a second flexible ligament 49 having a first end 51 connected to the first base and a second end 52 connected to the second base. The provision of the second flexible ligament is advantageous because the spinous processes have a proportionally larger dimension from the anterior to the posterior (thereby causing a posterior narrowing of the interspinous space). In addition, the provision of a second ligament distributes compressive extension loads more evenly along the processes.

In some embodiments, each base comprises a transverse hole 50 through passing through the side surface adapted for fixation to a side of a spinous process. The tranverse holes allows the surgeon to pass a fixation device (such as a screw) through each hole, thereby fixing the implant to the lower spinous process.

In some embodiments, the first ligament is made of a flexible polymer, and is preferably selected from the group consisting of polyester (preferably, Dacron®) and polyethylene. Preferably, the ligament is a longitudinal element having a thickness of between 3 cm and 8 cm. The selection of a thickness in this range, along with the selection of a flexible polymer as the material of construction, should provide a ligament that is suitably flexible to provide a gentle stop to extreme extension.

In other embodiments, the ligament takes the form of a fabric or strap. When the fabric embodiment is selected, it is desirable to use only a single ligament.

In some embodiments, the bases are made of a material selected from the group consisting of ultra high molecular weight polyethylene and PEEK. These materials are well known biocompatible materials of construction for load bearing medical devices.

Figure 4A:
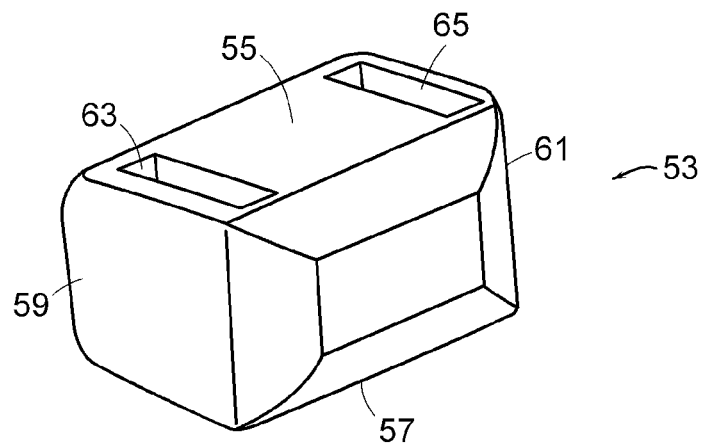
FIGS. 4a and 4b disclose components of a third embodiment of the present invention wherein the central body has axial openings adapted for the reception of extensions.
Figure 4B:
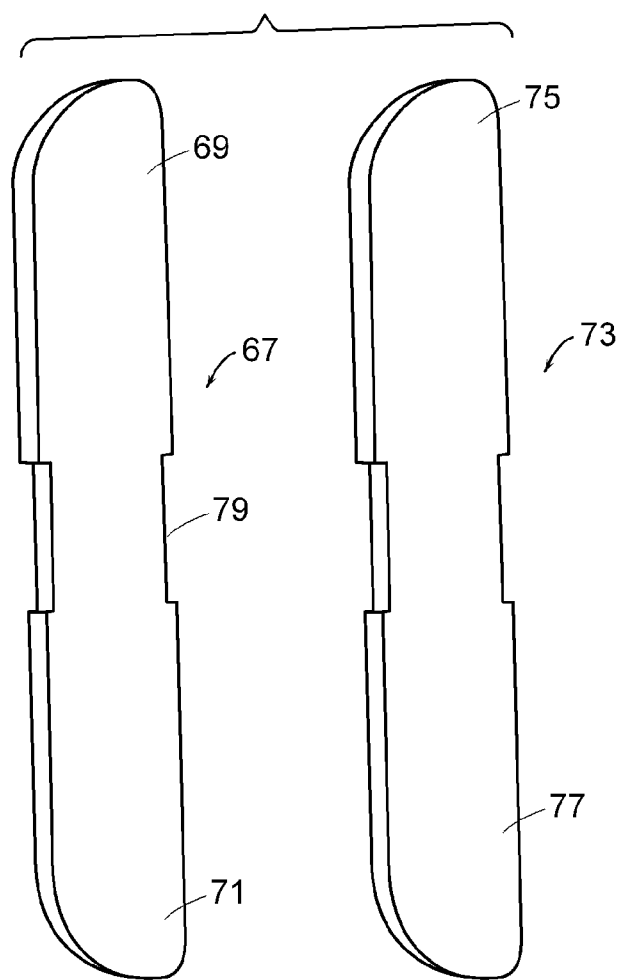
Figure 4C:
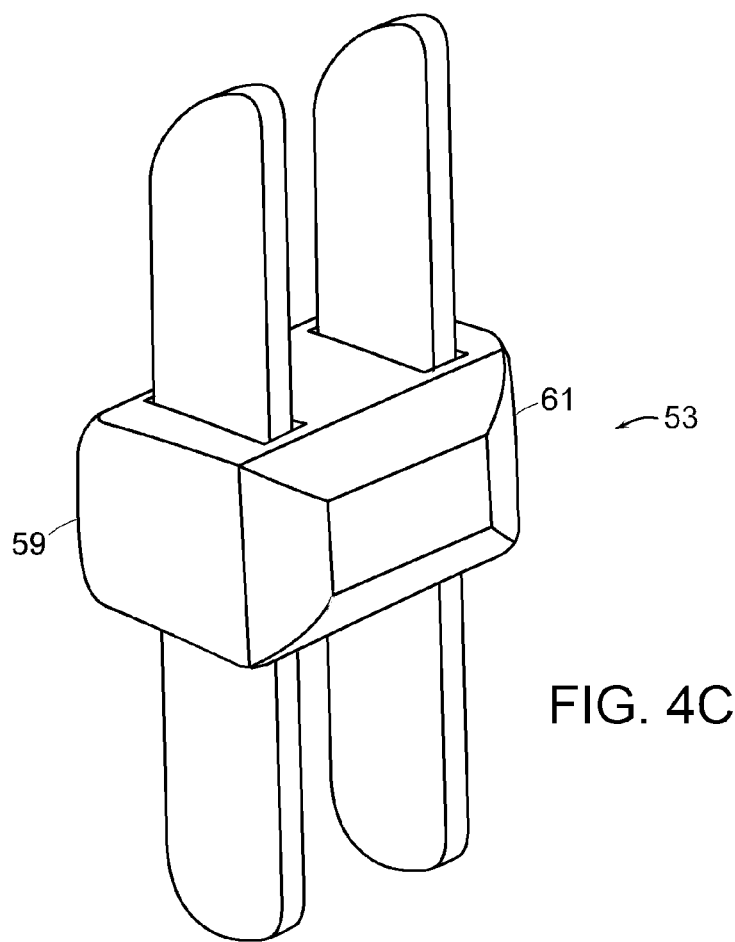
FIG. 4c shows the assembly of the components of FIGS. 4a and 4b.

Now referring to FIGS. 4a-c, there is provided an interspinous implant 51 for insertion into an interspinous space between a first and second spinous process, the implant comprising:
 a) a central body 53 having:
  i. an upper surface 55 for bearing against an upper spinous process, ii. a lower surface 57 for bearing against a lower spinous process,
iii. first 59 and second 61 side surfaces, and
iv. first 63 and second 65 axial through-holes, each through-hole extending from the upper surface to the lower surface,
b) a first extension 67 having an upper end 69 and a lower end 71, the first extension extending through the first axial through-hole of the central body,
c) a second extension 73 having an upper end 75 and a lower end 77, the second extension extending through the second axial through-hole of the central body,
wherein the upper ends of the extensions collectively define an upper bracket, and wherein the lower ends of the extensions collectively define a lower bracket.

In use, the surgeon first orients the central body portion of the implant so that its throughholes run in the (axial) saggital plane. The surgeon then inserts the oriented central body laterally into the interspinous space so that one axial throughhole is disposed on one side of the interspinous space and the second axial throughhole is disposed on the second side of the interspinous space. The surgeon then adjusts the position of the device so that it is approximately centered about each spinous process. The surgeon then inserts the extensions into the respective axial throughholes to secure the implant to the spinous processes.

Because neither extension is connected to the central body during insertion, but rather may be inserted separately, the physician can first view and assess the placement of the central body prior to adding the extensions without being visually shielded by the extension. In addition, the separate insertion of the extensions lowers the lateral span of the implant during insertion, thereby causing less damage to the sensitive musculature surrounding the interspinous space.

In addition, since the human spinous process is often a source of significant interindividual variation, each of the central body and extensions may be provided in different shapes and sizes, so that the surgeon can intra-operatively select the appropriate central body and extensions, thereby providing greater surface area contact between the implant and the adjacent processes and minimizing stresses. Different shapes (which, in some cases, have very small lateral profiles) may be suitable for different anatomical interspinous spaces. In addition, the central body may be provided in different heights so that the surgeon can select the central body producing the most appropriate degree of interspinous space distraction.

In some embodiments, the central body has a saggital profile comprising a substantially parallel anterior portion and an inwardly tapering posterior portion. It is believed that this profile more closely resembles the profile of the interspinous space, and so should provide for more contact therebetween and reduced stresses.

Since the physiologic loads experienced by central body during extension are relatively low (e.g., only about 20 pounds-force), the central body may be made of materials such as UWMWPE or PEEK. These materials are also preferred for the suitability in medical imaging procedures.

In some embodiments, the extensions comprise a centrally located recess 79 having a length substantially similar to the height of the central body. The recess allows the extension to snap into place when it is appropriately situated within the central body, thereby insuring a secure fit. When the extension is made of a metal material (such as a titanium alloy), the extension may further desirably comprise an internal slot (not shown) adapted to behave in a spring-like manner during extension insertion, thereby facilitating the insertion of the extension.

Figure 5A:
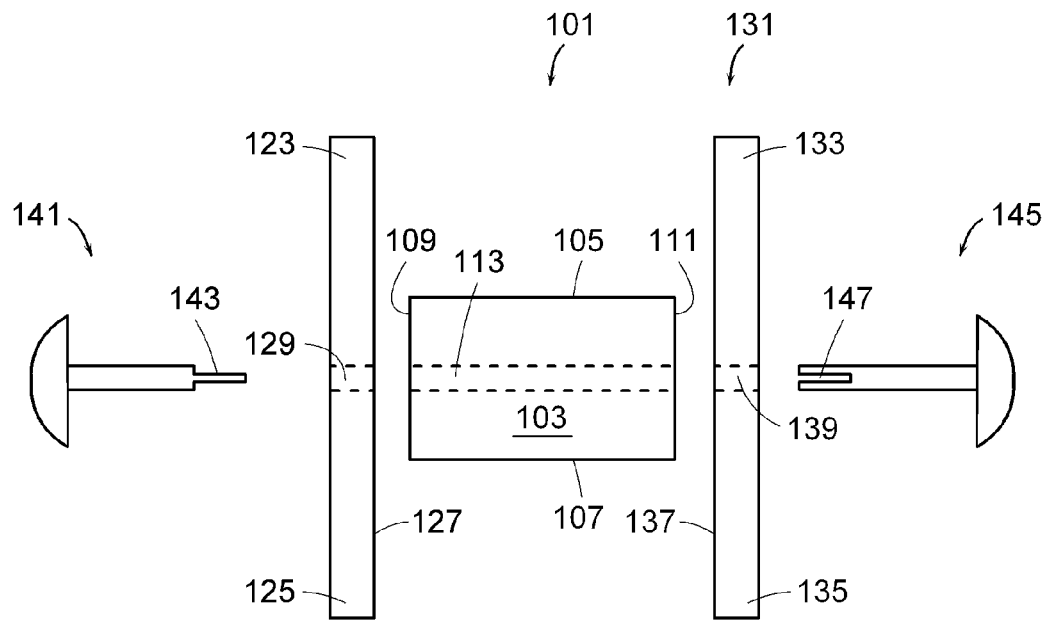
FIGS. 5a-5d disclose a fourth embodiment of the present invention wherein the central body and extensions are connected by rivets.

Now referring to FIG. 5a, there is provided an interspinous implant 101 for insertion into an interspinous space between a first and second spinous process, the implant comprising:
a) a central body 103 having:
i. an upper surface 105 for bearing against an upper spinous process,
ii. a lower surface 107 for bearing against a lower spinous process,
iii. first 109 and second 111 side surfaces defining a transverse axis, and
iv. a transverse 113 through-hole extending from the first side surface to the second side surface,
b) a first extension 121 having an upper end 123, a lower end 125, an inner surface 127, and a transverse throughhole 129, the inner surface of the first extension contacting the first side surface of the central body and aligning the transverse througholes,
c) a second extension 131 having an upper end 133, a lower end 135, an inner surface 137, and a tranverse throughhole 139, the inner surface of the second extension contacting the second side surface of the central body and aligning the transverse througholes, and
d) a rivet adapted to connect the extensions to the central body.
wherein the upper ends of the extensions collectively define an upper bracket, and
wherein the lower ends of the extensions collectively define a lower bracket.

In use, the surgeon first inserts the central body laterally into the interspinous space so that one opening of the tranverse throughhole is disposed on one side of the interspinous space and the second opening of the throughhole is disposed on the second side of the interspinous space. The surgeon then adjusts the position of the device so that it is approximately centered about each spinous process, and orients the central body portion of the implant so that its throughhole runs in the medial-lateral plane.

Next, the surgeon selects the appropriate extensions and places connecting pins through the throughholes of the extensions.

Figure 5B:
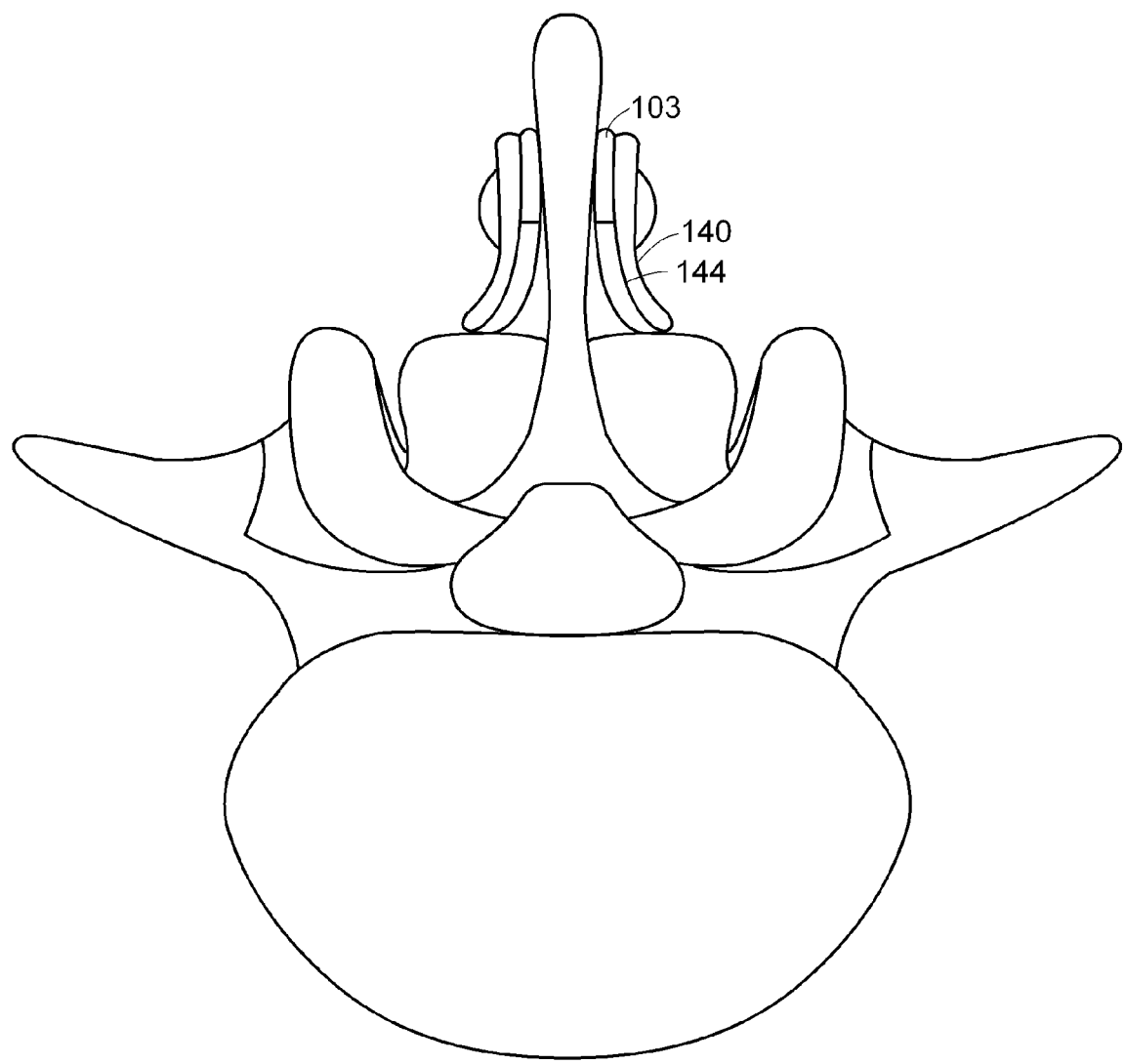

In some embodiments, as in FIG. 5b, the extensions are spaced from each other a distance that is substantially greater than the width of the spinous process. Since the supraspinous ligament should provide a tight grip upon the inserted central body, there should be no need for fastening the extensions to the spinous process. In this instance, the extensions merely serve as stops of excessive medial-lateral movement of the central body. Accordingly, providing a space between the side surfaces spinous processes and the inner surfaces of the extensions should minimize wear.

In some embodiments, the extensions have an inner surface 144 having a convex contour and an outer surface 140 having a concave contour. As shown in FIG. 5b, this convex contour is preferably adapted to match the contour of the spinous process. This contour should minimize wear of and stress upon the extension. The concave contour is preferably adapted to match the erector spinae portion of the low back musculature.

Figure 5C:
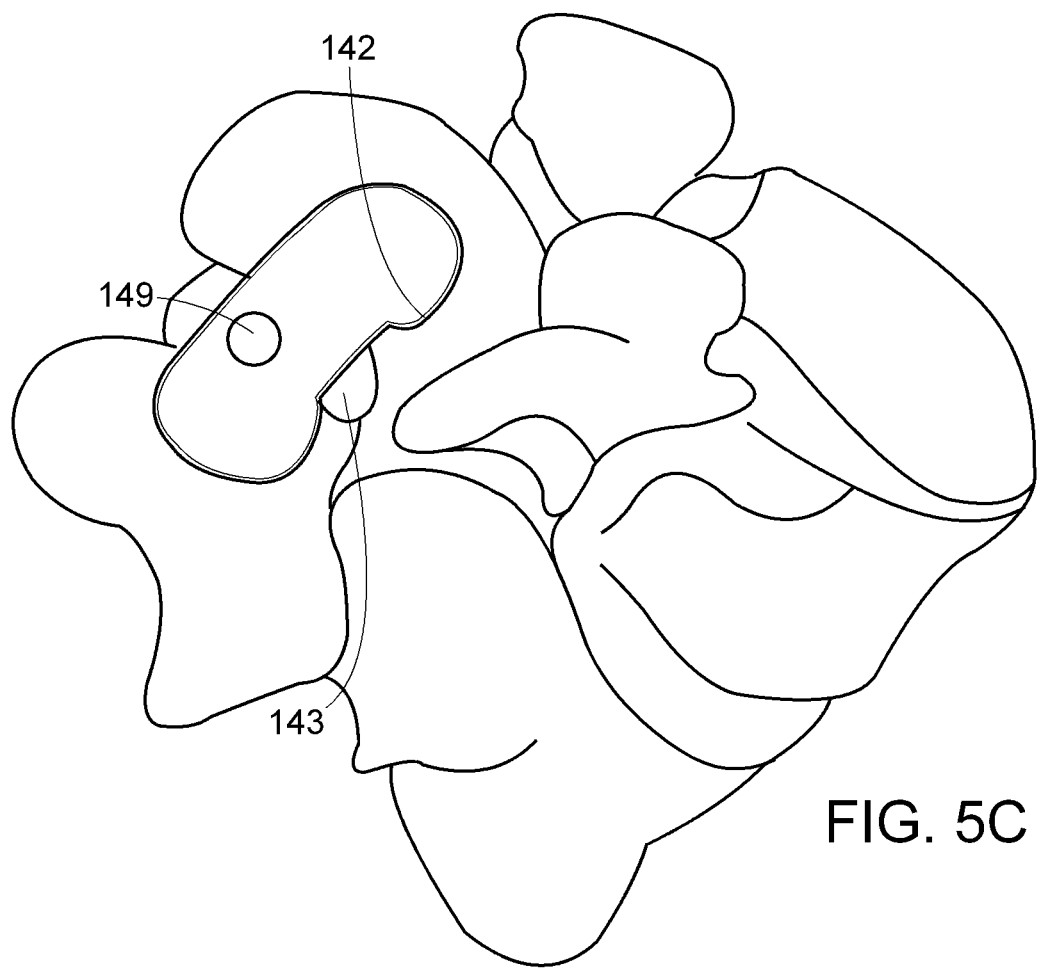

In some embodiments, the extensions have an anterior surface 142 having a concave contour 143. As shown in FIG. 5c, this concave contour is preferably adapted to match the convex contour of the lamina arch portion of the vertebral body. This contour should minimize wear of and stress upon the extension, and be less invasive to the patient's soft tissues.

Referring back to FIG. 5a, the rivet may include any conventional riveting assembly. In some embodiments, the rivet comprises:
i) a first connecting pin 141 adapted to fit in the first transverse throughole and having a male end 143, and
ii) a second connecting pin 145 adapted to fit in the second transverse throughole and having a female end 147.

In the embodiment shown in FIG. 5a, the rivets are shown as being separately constructed from the extensions. However, in other embodiments, the rivets may be integral with the extensions. Similarly, each side of the central body may be separately riveted to its respective extension.

Figure 5D:
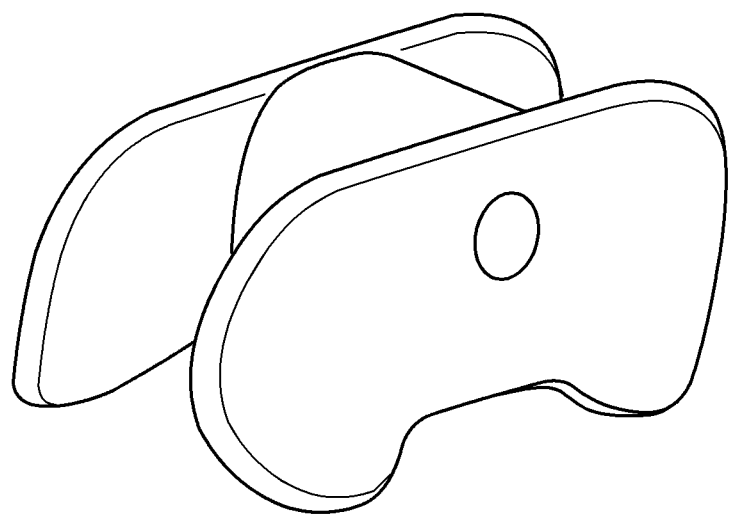

In some embodiments, as shown in FIG. 5d, the rivet is located about in the center of the extension. In other embodiments, as shown in FIG. 5c, the rivet 149 is located in the bottom half of the extension. It is believed that locating the rivet in the bottom half of the extensions desirably provides a good match fit with the bony contours of the vertebral body.

The implants of FIGS. 5a-d may be suitably manufactured from any suitable biomaterial, including metals such as titanium alloys, chromium-cobalt alloys and stainless steel) and polymers (such as PEEK, carbon fiber-polymer composites and UHMWPE. In preferred embodiments, the central body is made of UHMWPE (to provide moderate stiffness) and the extensions are made of a carbon fiber-PEEK composite (to provide stiffness to the extensions).

Figure 6C:
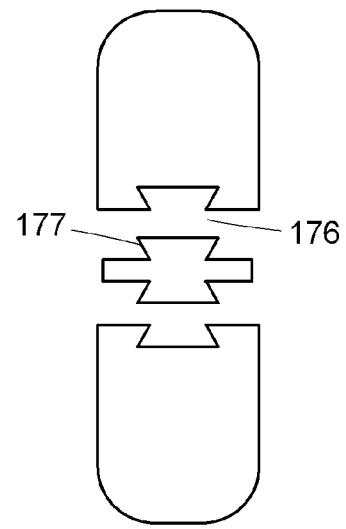
FIGS. 6a-6c disclose a fifth embodiment of the present invention having a pair of U-shaped hooks.
Figure 6B:
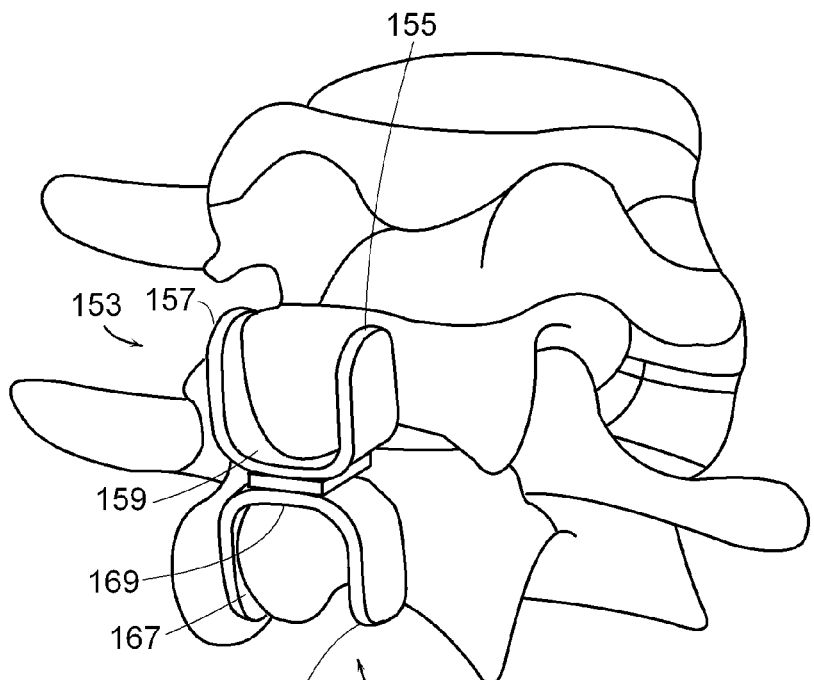
Figure 6A:
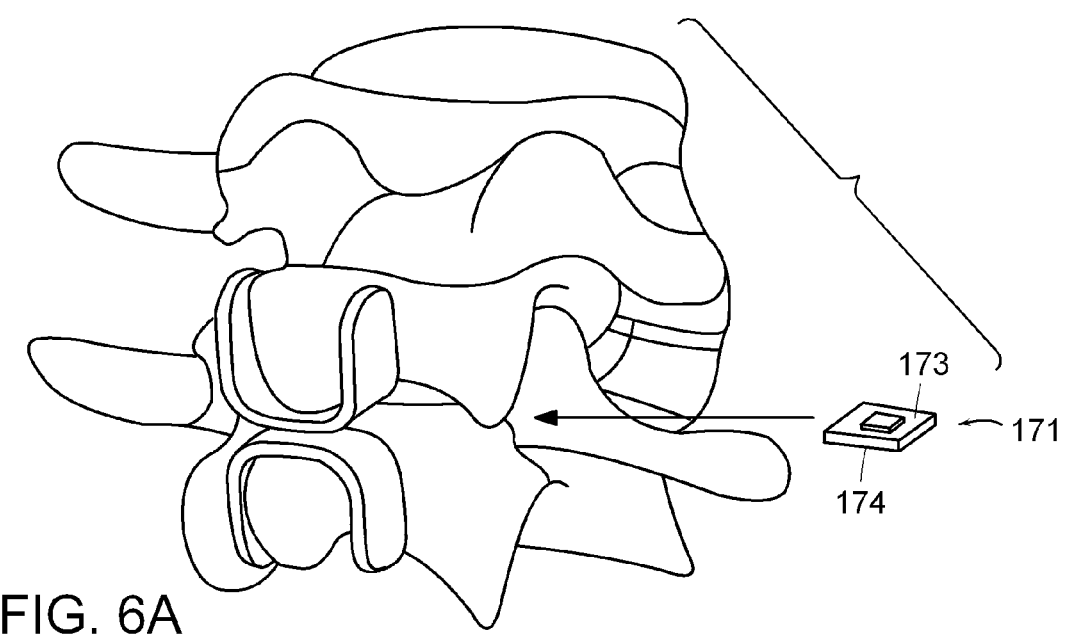

Now referring to FIGS. 6a-c, there is provided an interspinous implant 151 for insertion into an interspinous space between a first and second spinous process, the implant comprising:
a) an upper hook 153 having a leading end 155, a trailing end 157, an upper bearing surface 159 adapted to bear against the first spinous process, and a lower surface,
b) a lower hook 163 having a leading end 165, a trailing end 167, and a lower bearing surface 169 adapted to bear against the first spinous process, and an upper surface,
c) a central body 171 having:
   i. an upper surface 173 adapted for connection to the lower surface of the upper hook, and
   ii. a lower surface 174 adapted for connection to the upper surface of the lower hook.

Now referring to FIG. 6a, the surgeon simply inserts a leading base of the upper hook laterally into a first side of the interspinous space, and then pulls the leading end laterally and upward as it emerges from the second side of the interspinous space. The surgeon then repeats this process for the lower hook, so that each hooks envelops its respective side of the upper and lower spinous processes. The surgeon then inserts the central body into the space between the hooks and connects each hook to the central body, thereby fixing the implant. FIG. 6b shows the assembled implant.

In some embodiments, the leading and trailing ends of the upper hook extend in substantially a first same direction (more preferably, upward), and the leading and trailing ends of the lower hook extend in substantially a second same direction (more preferably, downward). In this condition, the profile of the implant is relatively low.

In some embodiments, the upper surface of the central body is adapted for connection to the lower surface of the upper hook by a male-female connection. In preferred embodiments, thereof the upper surface of the central body is adapted for connection to the lower surface of the upper hook by a dovetail connection 176. The dovetail connection is believed to produce a highly secure fixation.

In some embodiments, the upper surface of the central body has a female recess traversing the upper surface in a direction from the leading end to the trailing end. In others, the upper surface of the central body has a projection 177 traversing the upper surface in a direction from the leading end to the trailing end. In each of these cases, the orientation of the mating feature allows fixation to occur in the same motion as insertion of the central body. In preferred embodiments thereof, the upper surface of the central body has a dovetail feature traversing the upper surface in a direction from the leading end to the trailing end.

We claim:

1. An interspinous implant for insertion into an interspinous space between adjacent spinous processes, comprising:
a) a central body having an upper surface for bearing against an upper spinous process, a lower surface for bearing against a lower spinous process, and first and second side portions,
b) a first upper extension extending upward from the first side portions,
c) a second upper extension extending upward from the second side portion, the upper extensions collectively defining an upper bracket, and
d) a first lower extension extending downward from the first side portion,
e) a second lower extension extending downward from the second side portion, the lower extensions collectively defining a lower bracket,
wherein each of the first upper and first lower extensions comprises a shape memory metal,
wherein the implant is a unitary body,
wherein the first upper and first lower extensions are adapted to superelastically extend sideways in a martensitic phase, and
wherein the first upper and first lower extensions are adapted to extend upwards and downwards in an austenitic phase.

2. The implant of claim 1 wherein the first upper and first lower extensions are adapted to superelastically extend in a substantially parallel manner in a martensitic phase.

3. The implant of claim 2 wherein at least one of the first upper and first lower extensions has a chamfered end.

4. The implant of claim 2 wherein the upper and lower surfaces of the central body define a body height $H_{CB}$, wherein each of the first and second lower extensions have an end defining an extension height therebetween $H_E$, and wherein the extension height $H_E$ is less than the central body height $H_{CB}$.

5. The implant of claim 2 wherein the first upper and first lower extensions are adapted to extend in a substantially parallel manner in an austenitic phase.

6. The implant of claim 2 wherein the upper and lower surfaces of the central body have an anterior-posterior groove adapted to cradle the spinous processes.

7. The implant of claim 2 wherein the upper and lower surfaces of the central body are parallel.

8. The implant of claim 2 wherein the upper and lower surfaces of the central body are angled.

* * * * *